(12) United States Patent
Buckner et al.

(10) Patent No.: US 7,775,974 B2
(45) Date of Patent: Aug. 17, 2010

(54) FORCE-DETERMINING RETRACTION DEVICE AND ASSOCIATED METHOD

(75) Inventors: Gregory D. Buckner, Cary, NC (US); Gil Bolotin, Tel Aviv (IL)

(73) Assignee: North Carolina State University, Raleigh, NC (US)

( * ) Notice: Subject to any disclaimer, the term of this patent is extended or adjusted under 35 U.S.C. 154(b) by 291 days.

(21) Appl. No.: 11/187,207

(22) Filed: Jul. 22, 2005

(65) Prior Publication Data
US 2006/0025656 A1  Feb. 2, 2006

Related U.S. Application Data

(60) Provisional application No. 60/590,877, filed on Jul. 23, 2004.

(51) Int. Cl.
A61B 1/32 (2006.01)
(52) U.S. Cl. ............................. 600/202; 600/231
(58) Field of Classification Search ......... 600/201–202, 600/215, 219, 231–234
See application file for complete search history.

(56) References Cited

U.S. PATENT DOCUMENTS

| | | | |
|---|---|---|---|
| 2,013,892 A | 9/1935 | Lucas | |
| 3,008,239 A | 11/1961 | Lange | |
| 3,572,326 A | 3/1971 | Jensen | |
| 3,665,925 A | 5/1972 | Dersookian | |
| 3,785,381 A | 1/1974 | Lower et al. | |
| 3,789,849 A | 2/1974 | Laufe et al. | |
| 3,888,117 A | 6/1975 | Lewis | |
| 4,066,082 A | 1/1978 | Arcan et al. | |
| 4,155,355 A | 5/1979 | Yamamoto | |
| 4,254,763 A | 3/1981 | McCready et al. | |
| 4,297,884 A | 11/1981 | Leveque et al. | |
| 4,424,724 A | 1/1984 | Bookwalter et al. | |
| 4,432,376 A | 2/1984 | Huszar | |
| 4,784,150 A | 11/1988 | Voorhies et al. | |
| 4,899,761 A | 2/1990 | Brown et al. | |
| 4,945,896 A | 8/1990 | Gade | |
| 4,989,587 A | 2/1991 | Farley | |
| 5,020,933 A | 6/1991 | Salvestro et al. | |

(Continued)

OTHER PUBLICATIONS

Albin, M.D. et al., "Brain Retraction Pressure During Intracranial Procedures", *Surg. Forum.*, 1975, pp. 499-400, vol. 26.

(Continued)

*Primary Examiner*—Cris L Rodriguez
*Assistant Examiner*—Hao D Mai
(74) *Attorney, Agent, or Firm*—Womble Carlyle Sandridge & Rice, PLLC

(57) ABSTRACT

A retraction device including at least one pair of opposed retraction members, with each retraction member being capable of operably engaging the tissue to be retracted. A drive mechanism is operably engaged with at least one of each pair of retraction members for separating one of each pair of retraction members from the other to retract the tissue. A measuring device is operably engaged with at least one of the drive mechanism and one of each pair of retraction members, for determining and/or controlling a magnitude and/or rate of a force and/or strain imparted to the tissue by the drive mechanism via the retraction members as the tissue is being retracted. Associated devices and methods are also provided.

30 Claims, 4 Drawing Sheets

U.S. PATENT DOCUMENTS

| | | | |
|---|---|---|---|
| 5,184,601 A * | 2/1993 | Putman | 600/102 |
| 5,201,325 A | 4/1993 | McEwen et al. | |
| 5,213,112 A | 5/1993 | Niwa et al. | |
| 5,578,043 A | 11/1996 | Galstian | |
| 5,769,781 A | 6/1998 | Chappuis | |
| 6,730,021 B2 * | 5/2004 | Vassiliades et al. | 600/202 |
| 7,059,182 B1 * | 6/2006 | Ragner | 73/200 |
| 2003/0236472 A1 | 12/2003 | Van Hoeck et al. | |

OTHER PUBLICATIONS

Andrews, M.D. et al., "A Review of Brain Retraction and Recommendations for Minimizing Intraoperative Brain Injury", *Neurosurgery*, 1993, pp. 1052-1064, vol. 33, No. 6.

Bonfils-Roberts, E.A., "The Rib Spreader: A Chapter in the History of Thoracic Surgery", *Chest*, 1972, pp. 469-474, vol. 61, No. 5.

Datta et al., "Back Pain and Disability After Lumbar Laminectomy: Is There a Relationship to Muscle Retraction?", *Neurosurgery*, 2004, pp. 1413-1420, vol. 54, No. 6.

Evans, Krista, "The Hole-N-Ator: An Analysis of the Relation Between the Forces Applied to the Retracted Tissue and the Reactions Applied at the Crank Mechanism", 1999, http://em-ntserver.unl.edu:80/Mechanics-Pages/KristaEvans/holenator%20revised.htm.

Hongo et al., "Monitoring Retraction Pressure on the Brain", *J. Neurosurg*, 1987, pp. 270-275, vol. 66.

Kawaguchi, M.D. et al., "Back Muscle Injury After Posterior Lumbar Spine Surgery", *Spine*, 1994, pp. 2590-2597, vol. 19, No. 22.

Kawaguchi, M.D. et al., "Back Muscle Injury After Posterior Lumbar Spine Surgery", *Spine*, 1996, pp. 941-944, vol. 21, No. 8.

Kawaguchi, M.D. et al., "Back Muscle Injury After Posterior Lumbar Spine Surgery", *Spine*, 1996, pp. 2683-2688, vol. 21, No. 22.

Kawaguchi, M.D. et al., "Preventive Measures of Back Muscle Injury After Posterior Lumbar Spine Surgery", *Spine*, 1998, pp. 2282-2287, vol. 23, No. 21.

Styf, M.D. et al., "The Effects of External Compression by Three Different Retractors on Pressure in the Erector Spine Muscles During and After Posterior Lumbar Spine Surgery in Humans", *Spine*, 1998, pp. 354-358, vol. 23, No. 3.

Taylor et al., "The Impact of Self-Retaining Retractors on the Paraspinal Muscles During Posterior Spinal Surgery", *Spine*, 2002, pp. 2758-2762, vol. 27, No. 24.

Yokoh et al., "Intermittent Versus Continuous Brain Retraction", *J. Neurosurg.*, 1983, pp. 918-923, vol. 58.

* cited by examiner

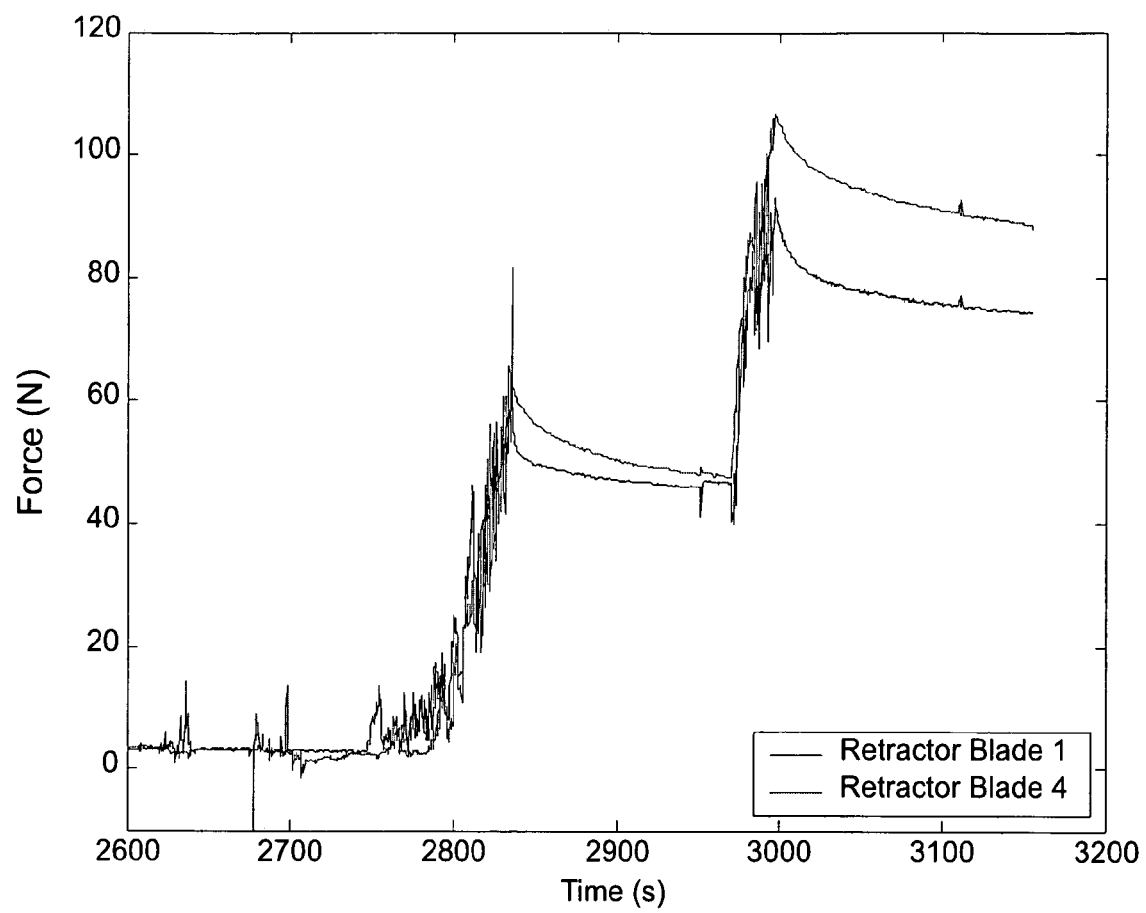
*FIG. 4:* Sternal Force Relaxation of 30% in 2 Minutes

FORCE-DETERMINING RETRACTION DEVICE AND ASSOCIATED METHOD

CROSS-REFERENCE TO RELATED APPLICATIONS

This application claims the benefit of U.S. Provisional Application No. 60/590,877, filed Jul. 23, 2004, which is incorporated herein in its entirety.

BACKGROUND OF THE INVENTION

1. Field of the Invention

The present invention relates to surgical devices and associated methods and, more particularly, to a tissue retraction device configured to determine, measure, and/or control the rate and/or magnitude of the force and/or strain applied or imparted to the tissue being retracted, and associated apparatus and method.

2. Description of Related Art

Some surgeries require opening a portion of the body so as to provide sufficient exposure of the subject of the procedure and to provide access for the physician to operate on the subject. For example, cardio-thoracic surgery requires opening the thoracic skeletal cavity in order to access the organs therein. Such access to the thoracic skeletal cavity may be gained through, for example, the sternum along the anterior midline, in a procedure known as a median sternotomy, or laterally between ribs, in a procedure known as a lateral thoracotomy. Once the appropriate incision(s) have been made into the cavity, the incision must be enlarged in order to allow access into the thoracic skeletal cavity. Such enlargement of the incision is often accomplished by a retraction device for separating the tissue surrounding the incision.

In some instances, however, the retraction device may exert significant forces on the tissue surrounding the incision, wherein such forces may sometimes adversely affect the tissue or any surrounding skeletal components. For example, during a median sternotomy, if the incised sternum is retracted too quickly, the sternum may completely fracture. As a result, the patient may require post-operative stabilization of the area, may experience a high level of post-operative pain, and may require an extended healing time. Some previous attempts at limiting such risks of partial stenotomies have included J-shape cuts at the mid-line of the sternum. However, such measures may also result in post operative instability of the sternal bone. In any instance, retraction may cause damage to the tissue surrounding the incision that can result in acute and chronic post operative pain to the patient, as well as other co-morbidities such as, for example, sternal dehesion, mediastenitis, lung atelectasis, pneumonia, or death. As one example, some studies report post-cardiac surgery pain (PCP) in about 80% of patients at three months post-operatively, and in about 28%-61% of patients at one to three years post-operatively.

Thus, there exists a need for a method and apparatus capable of determining a more optimal manner for accomplishing retraction of an incision, in procedures where such retraction is necessary for gaining access to a body cavity, in order to minimize trauma to the tissue surrounding the incision so as to, in turn, minimize post-operative stabilization requirements and post-operative pain, as well as to decrease the required healing time following such a procedure. Such a method and apparatus should also be applicable to determining and/or implementing a retraction procedure that provides the necessary access to body cavity while minimizing the discussed limitations or risks of a retraction procedure when such a situation is encountered.

BRIEF SUMMARY OF THE INVENTION

The above and other needs are met by the present invention which, in one embodiment, provides a retraction device adapted to retract tissue. Such a device comprises at least one pair of opposed retraction members, with each retraction member being capable of operably engaging the tissue to be retracted. A drive mechanism is operably engaged with at least one of each pair of retraction members for separating one of each pair of retraction members from the other to retract the tissue. A force-determining device is operably engaged with at least one of the drive mechanism and one of each pair of retraction members, for determining a force imparted to the tissue by the drive mechanism via the retraction members as the tissue is being retracted.

Another aspect of the present invention comprises a measuring assembly adapted to be used with a retraction device for retracting tissue. Such an assembly comprises at least one pair of opposed retraction members, with each retraction member being capable of operably engaging the tissue to be retracted. At least one of each pair of retraction members is adapted to operably engage a drive mechanism capable of separating one of each pair of retraction members from the other so as to retract the tissue. A measuring device is operably engaged with at least one of each pair of retraction members for determining a force imparted to the tissue via the retraction members as the tissue is being retracted.

Yet another aspect of the present invention comprises a method of retracting tissue. According to such a method, at least one pair of opposed retraction members is first operably engaged with the tissue to be retracted. A drive mechanism is then actuated, wherein the drive mechanism is operably engaged with at least one of each pair of retraction members, so as to separate one of each pair of retraction members from the other and retract the tissue. A force imparted to the tissue via the retraction members is then determined, as the tissue is being retracted, with a force-determining device operably engaged with at least one of the drive mechanism and one of each pair of retraction members.

Still another aspect of the present invention comprises a method of retracting tissue. According to such a method, at least one retraction member is operably engaged with the tissue to be retracted, and the tissue is retracted with the retraction member. A force imparted to the tissue via the retraction member is then determined, as the tissue is being retracted, with a force-determining device operably engaged with the retraction member.

Accordingly, embodiments of the present invention provide distinct advantages as further detailed herein.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 3:
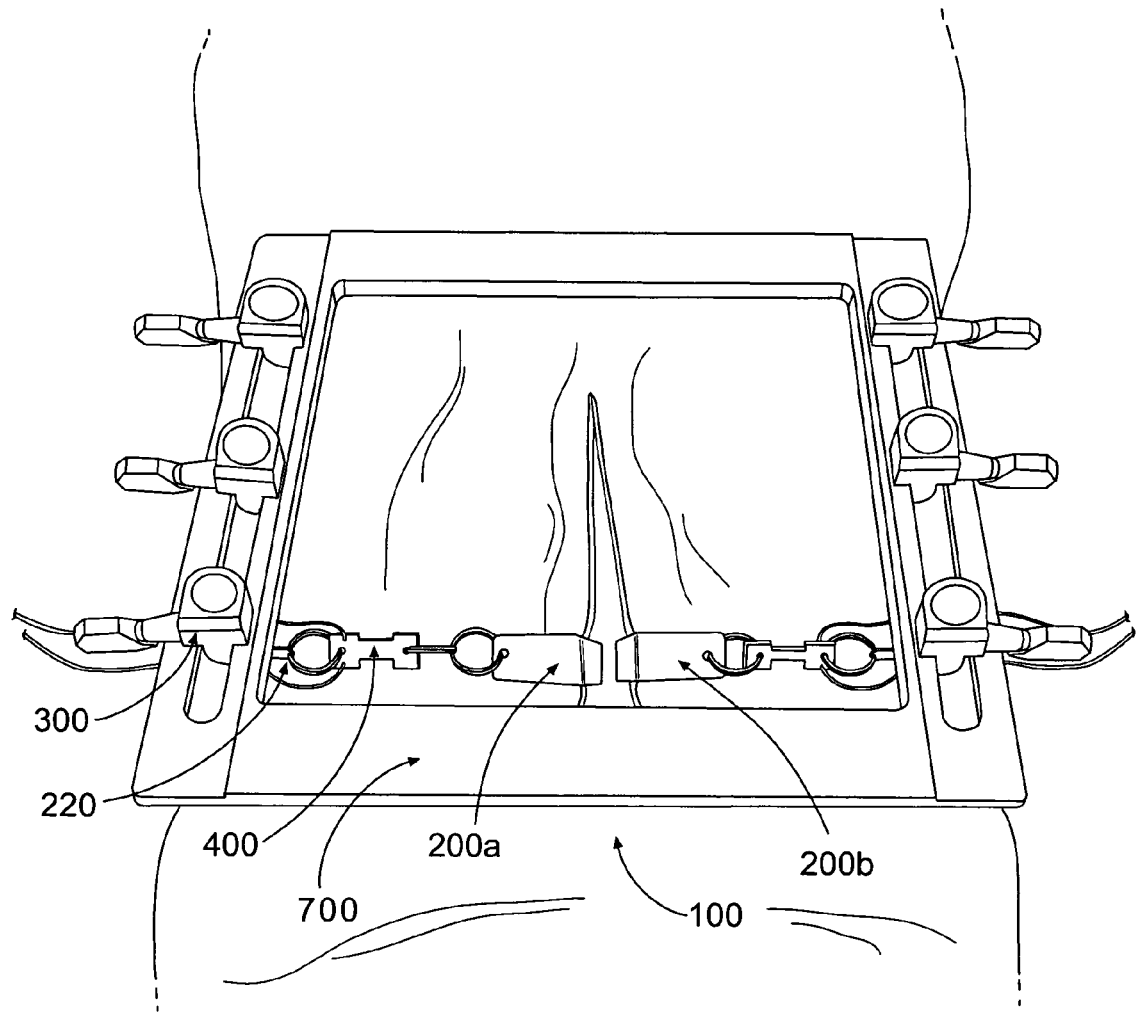

FIG. 3 is a perspective of a retraction device according to one embodiment of the present invention being applied in a retraction procedure and illustrates the separator blades interacting with the tissue about the incision; and FIG. 4 is a schematic graphical representation of measured force in the retraction device during a retraction procedure according to one embodiment of the present invention.

DETAILED DESCRIPTION OF THE INVENTION

The present inventions now will be described more fully hereinafter with reference to the accompanying drawings, in which some, but not all embodiments of the invention are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
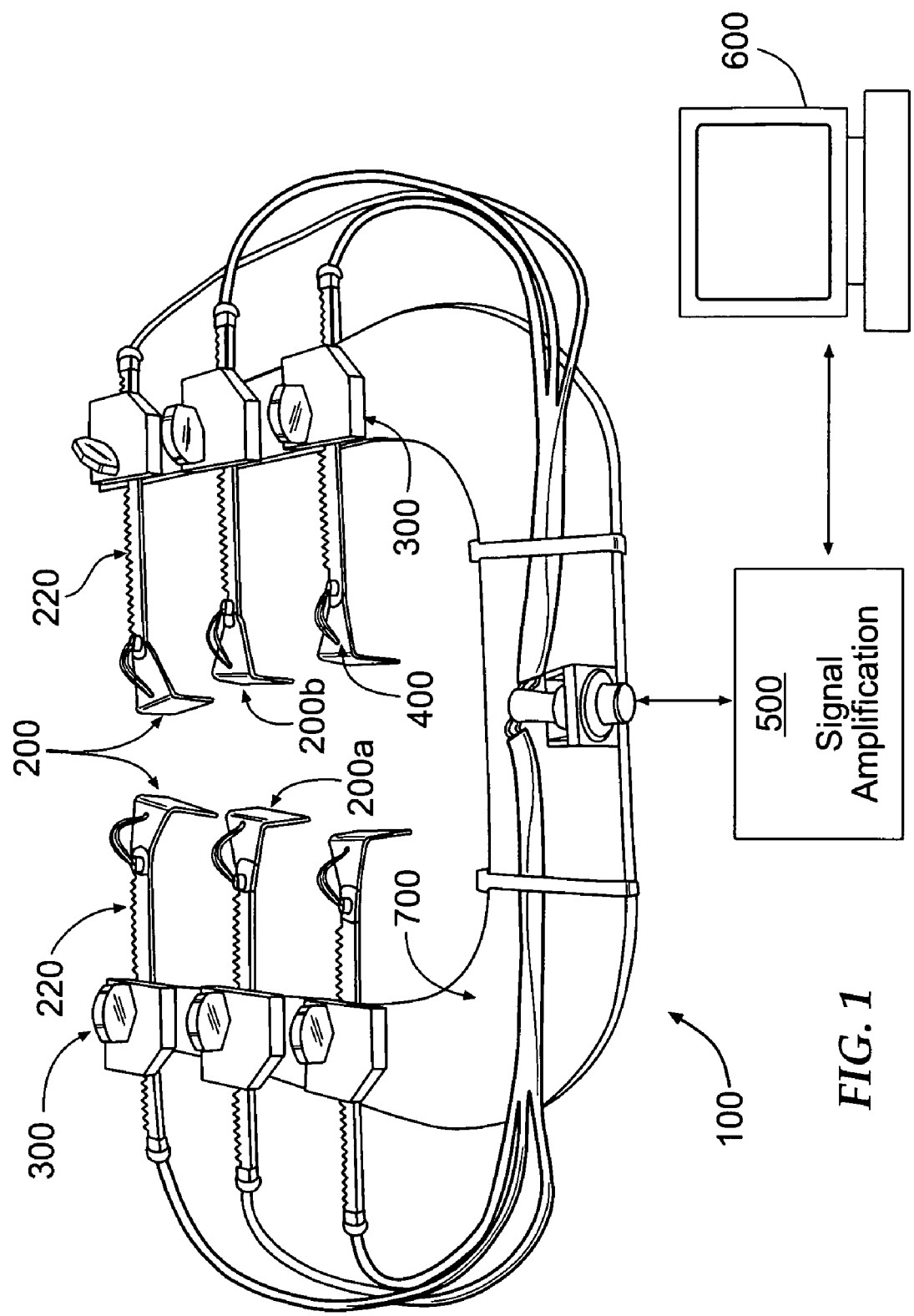
FIG. 1 is a schematic of a retraction device according to one embodiment of the present invention illustrating applied measuring devices in communication with a signal amplification/processing device and a computer device.
Figure 2A:
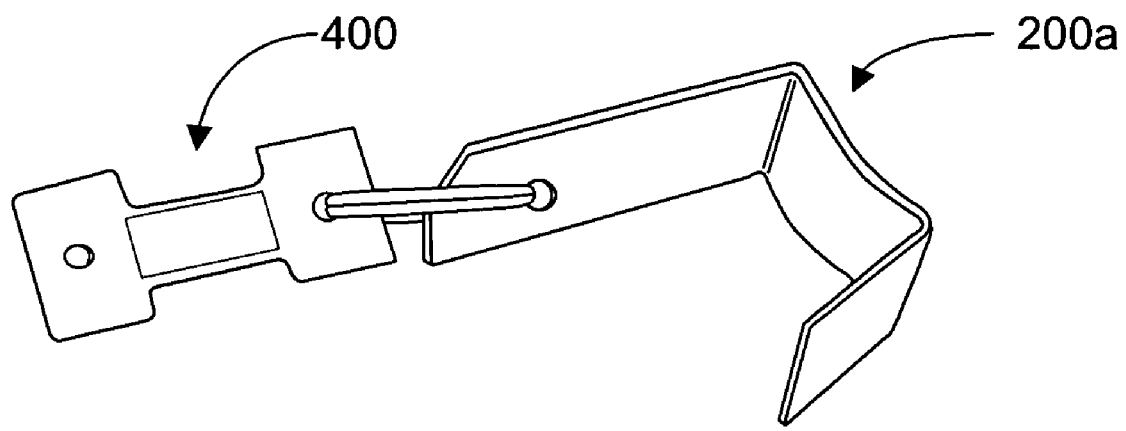
FIGS. 2A and 2B are schematics of different embodiments of a separator blade/measuring device used by a retraction device according to one embodiment of the present invention.
Figure 2B:
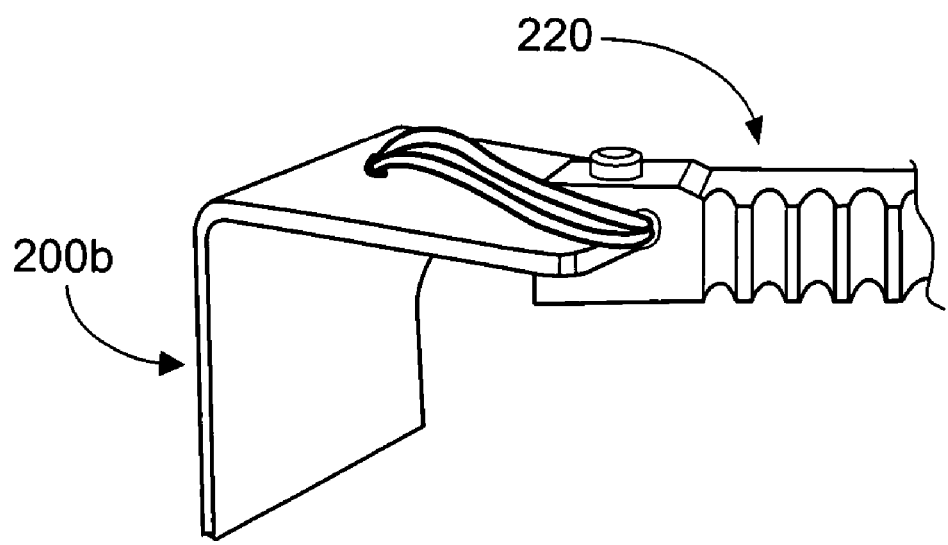

FIG. 1 illustrates a retraction device according to one embodiment of the present invention, the device being indicated generally by the numeral 100. Such a device 100 includes at least one pair of opposing retraction members 200, such as separator blades 200a, 200b (though three pairs of retraction members 200 are shown in FIG. 1, one skilled in the art will appreciate that the number of pairs of retraction members 200 may vary as necessary), and a separator mechanism 300 (also referred to herein as a "drive mechanism") operably engaged with either or both blades 200a, 200b and capable of separating the opposing blades 200a, 200b. The separator blades 200a, 200b, as further shown in FIGS. 2A and 2B, may each include an intermediary member 220 operably engaged with and extending between the respective separator blade 200a, 200b and the corresponding separator mechanism 300. In addition, the device 100 may also include a measuring device 400 (also referred to herein as a "force-determining device") operably engaged with at least one of the separator blades 200a, 200b, an intermediary member 220, and/or a separator mechanism 300 and, in one embodiment, is configured to measure a force, a stress, a strain, and/or a force-, stress-, or strain-rate exerted on the component and/or the retracted tissue and/or bone during a retraction procedure. One skilled in the art will appreciate that both bone and soft tissue may be affected during such a retraction procedure. However, for purposes of simplicity, bones and soft tissue may be referred to simply using the term "tissue," though such a term is not intended to be limiting in any manner with respect to the body components affected by a retraction procedure.

The measuring device 400 may comprise, for example, a strain gauge disposed serially between components or engaged in parallel, for example, by bonding, with one or more selected components, wherein such a strain gauge will be readily appreciated by one skilled in the art. In some instances, the strain gauge may be configured to produce a signal corresponding to a strain experienced thereby, wherein the strain may result from forces exerted between the separator blades 200a, 200b and the subject tissue surrounding an incision by the separator mechanism(s) 300 during the retraction process. The strain gauge presented herein as being one example of a measuring device 400 is not intended to be limiting in any manner with respect to the myriad of other measuring devices 400 that may be applied within the scope of the present invention. For example, the measuring device 400 may suitably comprise any mechanism capable of measuring the force imparted to the tissue during the retraction procedure.

Where the signal produced by the measuring device 400 is a low-level signal, the device 100 may also include a signal amplification device 500, as shown in FIG. 1, for amplifying the signal, as will be appreciated by one skilled in the art. Still further, embodiments of the device 100 may include a computer device 600 (otherwise referred to herein as a "processor device") for receiving the signal, whether amplified or not, for processing the signal into a usable format, and for storing raw and/or processed data. The computer device 600 may, in some instances, also comprise a controller device (not shown), for example, for controlling or otherwise interacting with the separator mechanism(s) 300 and/or the measuring device(s) 400. In some embodiments, the computer device 600 may include a communication interface (not shown) for allowing, for example, exportation of data or signals collected from the measuring device(s) 400, importation of parameters for controlling the separator mechanism(s) 300 and/or measuring device(s) 400, or communication with other peripheral equipment (not shown). In still other embodiments, the computer device 600, the measuring device(s) 400, and/or the separator mechanism(s) 300 may be operably engaged with or otherwise configured to communicate therebetween via a wireless communication system comprising one or more wireless communication devices.

In one embodiment, at least one of the intermediary members 220 operably engaged with one of the separator blades 200a, 200b may have at least a portion that is regularly toothed, the separator mechanism 300 being complementarily configured with respect to the toothed portion so as to be capable of gripping the same and moving the intermediary member 220 along an axis in, for example, a rack and pinion type relation. One skilled in the art will appreciate, however, that the intermediary member 220 and/or the corresponding separator blade 200a, 200b may be otherwise configured with respect to the separator mechanism 300 so as to allow the separator blade 200a, 200b to be moved along an axis, preferably oriented toward and away from the opposing separator blade 200a, 200b. For example, the intermediary member 220/separator mechanism 300 may be embodied in a hydraulic or electric actuator operably engaged with one of the separator blades 200a, 200b and capable of extending/retracting that separator blade 200a, 200b toward and away from the opposing separator blade 200a, 200b. As such, the embodiments illustrated and described herein are not intended to be limiting in any manner with respect to the scope of the present invention.

The separator blades 200a, 200b, intermediary members 220 (if present), and separator mechanism(s) 300 are, in some instances, operably engaged with a frame member 700 such that those components have a rigid framework across which to impart the force(s) for retracting the incision. As shown in FIG. 1, such a frame member 700 may comprise, for example, a generally "U" shaped member whereby the separator mechanism(s) 300 are engaged with each upright of the "U." The corresponding intermediary members 220 and separator blades 200a, 200b are engaged with the respective separator mechanisms 300 such that actuation of either or both of an opposing pair of separator mechanisms 300 at least causes separation of the appropriate pair of separator blades 200a, 200b. Where multiple pairs of separator blades 200a, 200b/separator mechanisms 300 are implemented, the respective pairs may be actuated individually or concurrently as desired and controllable at the separator mechanisms 300 or via the computer device 600 in communication therewith. In some instances, the frame member 700 may be configured to provide, or to cooperate with the separator blades 200a, 200b/separator mechanisms 300 to provide, a substantially uniform and steady stress that can be imparted in the retraction process via the separator mechanisms 300 and the separator blades 200a, 200b. One skilled in the art will appreciate that the retraction device 100 described herein in terms of separator blades 200a, 200b, separator mechanisms 300, and a frame member 700 will cover any number of such retraction devices, whether commercially available or not, and having various other features such as, for example, whether the device is configured to be disposable or re-usable, or whether the separator blades may comprise disposable components that can be used with a suitable non-disposable frame member. Accordingly, the disclosure of such a device herein is not intended to be limiting in any manner.

As shown in FIG. 3, the separator blades 200a, 200b are configured to be inserted into an incision so as to engage the tissue on either side of the incision. Once positioned, either or both of the separator mechanisms 300 may be actuated so as to move the respective separator blade 200a, 200b away from the incision so as to perform the retraction process since the separator mechanisms 300 are held in spaced apart relation by the frame member 700. The force imparted to the tissue via the separator blades 200a, 200b may have a different effect on the tissue based upon many factors such as, for example, the magnitude of the force, the rate at which the force is applied, the location and condition of the incision, and the physical structure of the tissue at the incision location. Accordingly, in one embodiment, the device 100 is configured so as to be capable of measuring and monitoring the force experienced by the separator blades 200a, 200b, and thus the force imparted to the tissue, in some instances, with the measuring and monitoring accomplished in real-time. The device 100 thus allows, for example, a partial incision through the sternal bone, and gradual retraction of the incision, while measuring the force imparted to the incised sternal bone. Preferably, the device 100 is capable of being controlled such that fracture or other damage of the incised tissue is avoided.

As such, embodiments of a retraction device 100 as disclosed herein may be used to perform empirical studies of incised tissue with various imparted or experienced forces, stresses, or strains, or rates thereof, while evaluating the effect thereof, during and after particular operative procedures requiring such a device 100 to be used. Such empirical studies may take into account many different tangible factors such as, for example, patient age, gender, physical characteristics, dimension of the incision(s), and/or location of the incision (s). Still further, non-tangible factors may also be considered such as, for example, required healing time, post-operative pain, or the like. In advantageous instances, such studies and the device 100 may allow, for example, minimally invasive approaches for some cardiac surgical procedures, without complete separation of the sternal bone or other tissue being retracted. That is, for instance, gradual retraction of the sternal bone with force monitoring as provided by the device 100 may provide a surgeon with real-time information as to what extent and at what rate that the incised bone can be retracted without causing fracture or other damage, thereby avoiding or minimizing drawbacks of such a procedure by minimizing required post-operative stabilization and post-operative pain, as well as decreasing the required healing time. Preliminary studies have shown, as presented in FIG. 4, that the applied retraction force or stress decreases according to a relaxation relation over time. In one instance, sternal bone forces showed about 30% relaxation in stress over a period of about 2 minutes, thereby indicating that gradual force-controlled retraction could facilitate an improved retraction procedure with reduced risk of fracture or other undesired separation. In another instance, peak forces were reduced by about 28.0%, average forces were reduced about 26.6%, and rib fractures were reduced from five to one, using force-controlled retraction during lateral thoracotomy on live sheep.

Upon analyzing the various parameters and results of such empirical studies, a retraction device 100 according to embodiments of the present invention may be particularly configured to receive or otherwise determine operational parameters for a surgical procedure in which the device 100 is to be applied and, upon actuation, automatically perform the desired retraction procedure according to, for example, the magnitudes or rates of the force, stress, strain, or other suitable criteria corresponding to the operational parameters. That is, for example, the parameters and results of such empirical studies may facilitate a control program housed by the computer device 600, whereby the computer device 600 may function as a controller device to actuate the separator mechanisms 300 according to the control program. More particularly, in such instances, when the device 100 is to be applied to a particular retraction procedure, the control program may prompt, via the computer device 600, for input of various parameters found to be determining factors in a retraction procedure. For example, the control program may require data about the patient, such as age and/or weight, details and location of the procedure, such as a dimension along the sternal bone, and the amount of access to the body cavity that is needed. Once the frame member 700 is in place and the separator blades 200a, 200b inserted into the incision, the device 100 may be actuated via the computer device 600 in order to automatically perform the retraction procedure using, for instance, the magnitudes or rates of the force, stress, strain, or other suitable criteria and, in some situations, possibly a relaxation time preceding a further force application, until the necessary separation of the incision is attained. One effect is preferably that the necessary retraction is attained without undesirable damage such as fracture or other separation of the tissue about the incision, thereby preserving or maintaining more optimal postoperative stability of the affected tissue. Such a device 100 may be applied, for example, to aortic valve surgical procedures performed through full sternotomies or partial sternotomies, as well as cardiac and mediastinal procedures, and lateral thoracotomy procedures. However, one skilled in the art will appreciate that such a list of potential applications is not intended to be limiting in any manner with respect to the myriad of possible applications of such a device 100.

Many modifications and other embodiments of the inventions set forth herein will come to mind to one skilled in the art to which these inventions pertain having the benefit of the teachings presented in the foregoing descriptions and the associated drawings. For example, the principles described herein may be extended to situations in which a measuring device 400 is applied to an existing retraction device 100 or a retraction tool, such as a discrete separator blade used independently of a retraction device 100 as described herein. In such instances, the measuring device 400 may be disposed between one of the separator blades and the tissue being retracted. In such a configuration, the measuring device 400, which may comprise a force-measuring device, will be capable of measuring the force between the separator blade and the tissue so as to provide suitable information with respect to, for example, the force, stress, strain, or rates thereof experienced by the tissue during the retraction procedure. Therefore, it is to be understood that the inventions are not to be limited to the specific embodiments disclosed and that modifications and other embodiments are intended to be included within the scope of the appended claims. Although That which is claimed:

1. A method of separating incised tissue, comprising:
    engaging at least one retraction member with the tissue at an incision having opposing sides to be separated;
    automatically separating the opposing sides of the incision by exerting a force thereon via the at least one retraction member as directed by a controller in operable communication therewith;
    measuring, via a measuring device in operable communication with the controller, at least one of a force magnitude, a stress magnitude, a strain magnitude, a force rate, a stress rate, and a strain rate associated with the exerted force on the tissue; and
    automatically effecting at least one of a force magnitude relaxation, a stress magnitude relaxation, a strain magnitude relaxation, a force rate relaxation, a stress rate relaxation, and a strain rate relaxation on the tissue in response to the measured at least one of the force magnitude, the stress magnitude, the strain magnitude, the force rate, the stress rate, and the strain rate via the at least one retraction member as directed by the controller.

2. A method according to claim 1, wherein automatically separating the opposing sides of the incision comprises automatically separating the incision at a separation rate.

3. A method according to claim 2, further comprising modifying the separation rate of the incision during the automatically separating of the opposing sides of the incision.

4. A method according to claim 3, wherein modifying the separation rate during the automatically separating of the opposing sides of the incision comprises increasing the separation rate during the automatically separating of the sides of the incision.

5. A method according to claim 4, wherein increasing the separation rate during the automatically separating of the sides of the incision further comprises increasing the separation rate in relation to the measured at least one of the force magnitude, the stress magnitude, the strain magnitude, the force rate, the stress rate, and the strain rate associated with the exerted force on the tissue, resulting from the automatically separating of the sides of the incision.

6. A method according to claim 3, wherein modifying the separation rate comprises decreasing the separation rate during the automatically separating of the sides of the incision.

7. A method according to claim 6, wherein decreasing the separation rate further comprises decreasing the separation rate in relation to the measured at least one of the force magnitude, the stress magnitude, the strain magnitude, the force rate, the stress rate, and the strain rate.

8. A method according to claim 3, wherein the modifying the separation rate comprises modifying the separation rate in relation to the measured at least one of the force magnitude, the stress magnitude, the strain magnitude, the force rate, the stress rate, and the strain rate associated with the exerted force on the tissue, resulting from the automatically separating of the sides of the incision.

9. A method according to claim 1, further comprising further automatically separating the opposing sides of the incision after the automatically effecting of a relaxation of the tissue.

10. A method according to claim 9, wherein further automatically separating the opposing sides of the incision further comprises further automatically separating the opposing sides of the incision in relation to the measured at least one of the force magnitude, the stress magnitude, the strain magnitude, the force rate, the stress rate, and the strain rate associated with the exerted force on the tissue, resulting from the automatically separating of the sides of the incision.

11. A method according to claim 1, wherein automatically separating the opposing sides of the incision by exerting a force thereon comprises communicating a drive signal to at least one drive mechanism operably engaged with at least one retraction member operably engaged with the tissue, such that the at least one retraction member provides the exerted force to separate the opposing sides of the incision.

12. A method according to claim 1, wherein automatically separating the opposing sides of the incision further comprises automatically separating the opposing sides of the incision in relation to at least one operational parameter input by a user into an interface.

13. A method according to claim 1, wherein the steps of automatically separating the opposing sides of the incision and automatically effecting a relaxation are performed before a desired separation of the opposing sides of the incision is attained.

14. A method according to claim 13, wherein the step of automatically separating the opposing sides of the incision is further performed after the step of automatically effecting a relaxation before the desired separation of the opposing sides of the incision is attained.

15. A method according to claim 13, wherein the steps of automatically separating the opposing sides of the incision and automatically effecting a relaxation are repeatedly performed until the desired separation of the opposing sides of the incision is attained.

16. A system for separating incised tissue, comprising:
    at least one retraction member capable of operably engaging tissue at a side of an incision having opposing sides, and the at least one retraction member being configured to exert a force on the tissue to separate the opposing sides of the incision;
    a drive mechanism operably engaged with the at least one retraction member and configured to actuate the at least one retraction member to exert the force in response to a drive signal, such that a separation of the opposing sides of the incision is capable of being performed automatically by the at least one retraction member;
    a measuring device operably engaged with the drive mechanism and configured to provide a measure signal corresponding to at least one of a force magnitude, a stress magnitude, a strain magnitude, a force rate, a stress rate, and a strain rate associated with the exerted force on the tissue at the side of the incision by the at least one retraction member as the opposing sides of the incision are being separated; and
    a controller operably coupled to the drive mechanism and the measuring device, the controller being configured to:
        communicate the drive signal to the drive mechanism to automatically actuate the at least one retraction member to exert the force on the tissue to automatically separate the opposing sides of the incision;
        receive the measure signal from the measuring device corresponding to at least one of the force magnitude, the stress magnitude, the strain magnitude, the force rate, the stress rate, and the strain rate associated with the exerted force on the tissue, resulting from separating the opposing sides of the incision; and
        automatically effect at least one of a force magnitude relaxation, a stress magnitude relaxation, a strain magnitude relaxation, a force rate relaxation, a stress rate relaxation, and a strain rate relaxation on the tissue via the at least one retraction member in response to the measured at least one of the force magnitude, the stress magnitude, the strain magnitude, the force rate, the stress rate, and the strain rate.

17. A system according to claim 16, wherein the controller is configured to separate the opposing sides of the incision at a separation rate.

18. A system according to claim 17, wherein the controller is further configured to modify the separation rate of the tissue during automatic separation of the opposing sides of the incision.

19. A system according to claim 18, wherein the controller is further configured to modify the separation rate of the opposing sides of the incision by increasing the separation rate of the opposing sides of the incision during the automatically performed separation of the opposing sides of the incision.

20. A system according to claim 18, wherein the controller is further configured to modify the separation rate of the opposing sides of the incision by decreasing the separation rate of the opposing sides of the incision during the automatically performed separation of the opposing sides of the incision.

21. A system according to claim 18, wherein the controller is further configured to modify the separation rate of the opposing sides of the incision in relation to the measured at least one of the force magnitude, the stress magnitude, the strain magnitude, the force rate, the stress rate, and the strain rate associated with the exerted force on the side of the incision, resulting from the automatically performed separation of the opposing sides of the incision.

22. A system according to claim 16, wherein the controller is further configured to further automatically perform separation of the opposing sides of the incision after automatically effecting a relaxation on the tissue.

23. A system according to claim 22, wherein the controller is further configured to perform the further automatically performed separation of the opposing sides of the incision in relation to the measured at least one of the force magnitude, the stress magnitude, the strain magnitude, the force rate, the stress rate, and the strain rate associated with the exerted force at the side of the incision, resulting from the automatically performed separation of the opposing sides of the incision.

24. A system according to claim 16, wherein the controller is further configured to automatically separate the opposing sides of the incision in relation to at least one operational parameter input by a user into an interface.

25. A system according to claim 24, wherein the at least one operational parameter is selected from the group consisting of force, stress, strain, force rate, stress rate, strain rate, empirically-determined data, data about a patient, age of a patient, weight of a patient, information about a procedure to be performed on a patient, location of a procedure to be performed on a patient, dimensions of a sternal bone of a patient, and an amount of access to a body cavity of a patient.

26. A system according to claim 16, further comprising a wireless communication device operably engaged with the measuring device and configured to communicate the measure signal wirelessly, wherein the controller is further configured to receive the measure signal from the wireless communication device.

27. A system according to claim 16, further comprising a display in communication with one of the controller and the measuring device, and configured to display the measured at least one of the force magnitude, the stress magnitude, the strain magnitude, the force rate, the stress rate, and the strain rate associated with the exerted force on the tissue, resulting from the automatically performed separation of the opposing sides of the incision.

28. A system according to claim 16, wherein the controller is configured to communicate the drive signal to the drive mechanism to actuate the at least one retraction member to exert the force on the side of the incision and automatically effect the relaxation on the side of the incision before a desired separation of the opposing sides of the incision is attained.

29. A system according to claim 28, wherein the controller is further configured to communicate the drive signal to the drive mechanism to actuate the at least one retraction member to exert the force on the side of the incision after automatically effecting the relaxation on the side of the incision before the desired separation of the opposing sides of the incision is attained.

30. A system according to claim 28, wherein the controller is further configured to communicate the drive signal to the drive mechanism to actuate the at least one retraction member to exert the force on the side of the incision and automatically effect the relaxation on the side of the incision repeatedly until the desired separation of the opposing sides of the incision is attained.

* * * * *